US006810282B2

(12) United States Patent
Taha et al.

(10) Patent No.: US 6,810,282 B2
(45) Date of Patent: Oct. 26, 2004

(54) METHOD AND APPARATUS FOR DYNAMICALLY SELECTING AN ELECTROCARDIOGRAM COMPRESSION PROCESS BASED ON COMPUTERIZED ANALYSIS OF CARDIAC RHYTHM AND CONTOUR

(75) Inventors: Basel H. Taha, Menomonee Falls, WI (US); Shankara B. Reddy, Cedarburg, WI (US); Joel Q. Xue, Germantown, WI (US); Paul P Elko, River Hills, WI (US)

(73) Assignee: GE Medical Systems Information Technolgies, Inc., Milwaukee, WI (US)

( * ) Notice: Subject to any disclaimer, the term of this patent is extended or adjusted under 35 U.S.C. 154(b) by 402 days.

(21) Appl. No.: 09/682,856

(22) Filed: Oct. 25, 2001

(65) Prior Publication Data

US 2003/0083581 A1 May 1, 2003

(51) Int. Cl.[7] ................................................. A61B 5/04
(52) U.S. Cl. ....................................................... 600/509
(58) Field of Search ................................. 600/509, 510, 600/515–525; 607/5, 6; 714/11, 12

(56) References Cited

U.S. PATENT DOCUMENTS 5,209,229 A * 5/1993 Gilli ............................... 607/5
5,810,014 A 9/1998 Davis et al.

6,347,245 B1 * 2/2002 Lee et al. ..................... 600/523

FOREIGN PATENT DOCUMENTS

WO WO 98/39699 9/1998

OTHER PUBLICATIONS

Sateh M. S. Jalaleddine, Chriswell G. Hutchens, Robert D. Strattan and William A. Coberly, "ECG Data Compression Techniques—A Unified Approach," *IEEE Transactions on Biomedical Engineering*, vol. 37, No. 4, Apr. 1990, pp. 329–343, USA.

B. R. Shankara Reddy, Ph.D., David W. Christenson, G. Ian Rowlandson, Christoph Zywietz, Thomas Sheffield, M.D., and Christian Brohet, M.D., "Data Compression for Storage of Resting ECGs Digitized at 500 Samples/Second," reprinted from *Biomedical Instrumentation & Technology*, Mar./Apr. 1992, pp. 133–149, published by Hanley & Belfus, Inc., Philadelphia, PA, USA.

* cited by examiner

Primary Examiner—George Manuel
(74) Attorney, Agent, or Firm—Andrus, Sceales, Starke & Sawall, LLP

(57) ABSTRACT

A method of automatically selecting a physiological data manipulation process. After raw data including an asynchronous component having diagnostic information and including a synchronous component is received, the asynchronous component is separated from the synchronous component. A data manipulation process based on the diagnostic information is automatically selected based on the signal conditions generated during an analysis process.

44 Claims, 2 Drawing Sheets

METHOD AND APPARATUS FOR DYNAMICALLY SELECTING AN ELECTROCARDIOGRAM COMPRESSION PROCESS BASED ON COMPUTERIZED ANALYSIS OF CARDIAC RHYTHM AND CONTOUR

BACKGROUND OF INVENTION

The invention relates to a computerized electrocardiography system and signal processing therefor. More specifically, this invention relates to the compression of electrocardiographic data for permanent storage and for transmission between an ECG acquisition device and an ECG management system or between two ECG devices.

The electrocardiogram (ECG) is a very commonly used, simple, non-invasive test to asses a patient's cardiac condition. Each year millions of ECGs (resting, ambulatory, exercise, bedside monitoring, telemetry, etc.) are collected from patients and are stored on ECG management and cardiovascular information systems. Although ECG records are relatively small in size in comparison with diagnostic imaging modalities such as CT and MRI, the large number of ECGs that are collected and managed in large hospitals can place a significant demand on storage space.

The large requirement for storage area generates two significant problems. First, the storage device (such as a disk drive) must be large enough to store a large number of ECGs. Second, and more importantly, the communication devices coupling multiple systems are relatively slow, compared to the processing capabilities of the computerized systems. Thus, the time required to transmit a large number of ECGs between computer systems can be significant.

One technique used to solve both of these problems is that of data compression. Utilizing data compression techniques, the storage size of the ECG is reduced. Thus, the ECG utilizes a smaller amount of space in the storage device, and can be transmitted via a communication link more quickly and reliably.

Two types of ECG compression techniques exist: lossless compression and lossy compression. In lossless compression, the storage size of the ECG is reduced without losing any information in the original data. That is, the ECG can be compressed using lossless compression, stored or transmitted, then decompressed, and the decompressed ECG will be identical to the original ECG. In lossy compression, however, the size of the ECG is reduced and a certain amount of data loss occurs. Thus, an ECG which is compressed, stored or transmitted, and then decompressed will be somewhat different from the original ECG. Although lossy compression causes some data loss, that data loss in most clinical ECGs is either not apparent to the user, or presumed to be inconsequential to cardiac diagnosis. Indeed, lossy compression has been used and appreciated in clinical practice for many years.

By its nature, the ECG has a high degree of repetition within its data. This repetitive nature has been exploited to develop highly efficient compression schemes. These schemes decompose the ECG into its synchronous (or repeating) and asynchronous (non-repeating) components. The synchronous component of the ECG, typically consisting of a cardiac cycle with its P-QRS-T features, is then reduced to a single representative pattern via averaging or medianization of the sample data. (Not all waves necessarily need to be present in a cardiac cycle. A repeating pattern of QRS-T waves or QRS complexes are occasionally seen in some cardiac rhythms.) The median (or average) P-QRS-T complex is subtracted from the original (raw) ECG data. The remainder, asynchronous component, typically has a narrow dynamic range and lends itself to efficient compression. Given the narrow dynamic range of the asynchronous component, additional compression efficiency can be gained through low-pass filtering, down-sampling and re-quantization of the data. If performed, these last steps render the compression lossy. Both the synchronous and asynchronous components are then compressed using an encoding scheme such as Huffman encoding. Lossy compression ratios as high as 20:1 have been reported using this method.

SUMMARY OF INVENTION

The above compression method derives its efficiency from two major premises. One is that the ECG has a large degree of repetition of nearly identical patterns, and two is that the asynchronous component has a narrow dynamic range of voltages compared to the overall ECG data. Both premises, but particularly the latter, are critically dependent on the ability to accurately detect, classify and delineate the repeating pattern within the ECG and certain characteristics of the ECG waveforms. Even a slight imprecision in delineating a particular cycle of the repeating pattern containing high frequency components may leave a high-frequency, large-amplitude pattern in the asynchronous component of the ECG. For example, paced ECGs may leave a large pacing artifact in the asynchronous component at a location where a cardiac cycle was slightly misaligned with the representative cycle. In lossy compression, the amplitude of this narrow pacing artifact can be severely reduced by low-pass filtering, down-sampling and re-quantization causing the reconstructed ECG to be drastically different from the original. In addition, ECGs with high ventricular rates and those with small P waves can pose similar challenges to the lossy compression scheme.

Obviously, employing a lossless compression scheme would solve the problem described above. However, there would be an approximately three-fold increase in storage requirements if lossless compression was applied universally for all acquired ECGs. This additional storage requirement adds a great deal of expense and is a very high price to pay for solving the problem given that the overwhelming majority of ECGs do not pose any problems with the high-efficiency lossy compression.

An approach for selecting between lossy and lossless ECG compression is to allow the system user to select between the two methods of compression. Besides the obvious inconvenience to the user, this approach requires a certain level of understanding by the user of which technique works best in each situation. In addition, the speed of the system is decreased due to the decision time of the user. One goal of compression is to increase the speed of data storage and transmission; thus, the time required by the user to select a compression technique hinders attaining this goal.

Accordingly, the invention provides a method of selecting a physiological data manipulation process. The method of selecting a physiological data manipulation process includes the acts of receiving raw data including an asynchronous component having diagnostic information and including a synchronous component, separating the asynchronous component from the synchronous component, and selecting a data manipulation process based on the diagnostic information.

In one embodiment, the selection of a physiological data manipulation process includes classifying an abnormality condition of the diagnostic information. The act of classifying the abnormality condition further includes analyzing a rhythm, for example a sinus rhythm, an atrio-ventricular conduction, a ventricular rate, a P wave amplitude, a QT interval and an age qualifier from the diagnostic information.

In still another embodiment, the data manipulation process includes processing the raw data using the lossy process or the lossless process.

In still another embodiment, the separation of the asynchronous component from the synchronous component includes generating a data condition of the diagnostic information.

The invention further provides a medical device. The medical device includes a patient data acquisition device that collects physiological data including an asynchronous component having diagnostic information and a synchronous component. The medical device also includes a software program for selecting a method of processing the physiological data, and for manipulating the physiological data based on the method of processing the physiological data selected. The software program has a signal separation module that receives the data from the data collection and separates the asynchronous component from the synchronous component, a selector module that generates a data manipulation process selection based on the diagnostic information, and a data manipulator module that manipulates the asynchronous component and the synchronous component according to the component type and the data manipulation process selection of the selector module.

In one embodiment, the software program further includes a classifier module to classify an abnormality condition of the diagnostic information. In still another embodiment, the software program further includes a generator module to generate a data condition of the diagnostic information.

It is a principal advantage of the invention to provide a medical device and a method of selecting a physiological data manipulation process for compression of ECGs with certain cardiac conditions.

It is another advantage of the invention to provide a medical device and a method of selecting a physiological data manipulation process that is fully automated.

It is another advantage of the invention to provide a medical device and a method of selecting a physiological data manipulation process that requires little or no change to the currently-implemented decompression algorithm in ECG storage systems.

It is another advantage of the invention to provide a medical device and a method of selecting a physiological data manipulation process that is configurable by the users of the system.

It is another advantage of the invention to provide a medical device and a method of selecting a physiological data manipulation process in which development and implementation can be accomplished fairly quickly at a low cost.

It is another advantage of the invention to provide a medical device and a method of selecting a physiological data manipulation process that is transparent to users since it requires no interface changes.

It is another advantage of the invention to provide a medical device and a method of selecting a physiological data manipulation process that reduces customer complaints leading to support cost savings.

Other features and advantages of the invention will become apparent to those skilled in the art upon review of the following detailed description, claims, and drawings.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of including and comprising and variations thereof herein is meant to encompass the items listed thereafter and equivalents thereof as well as additional items.

Figure 1:
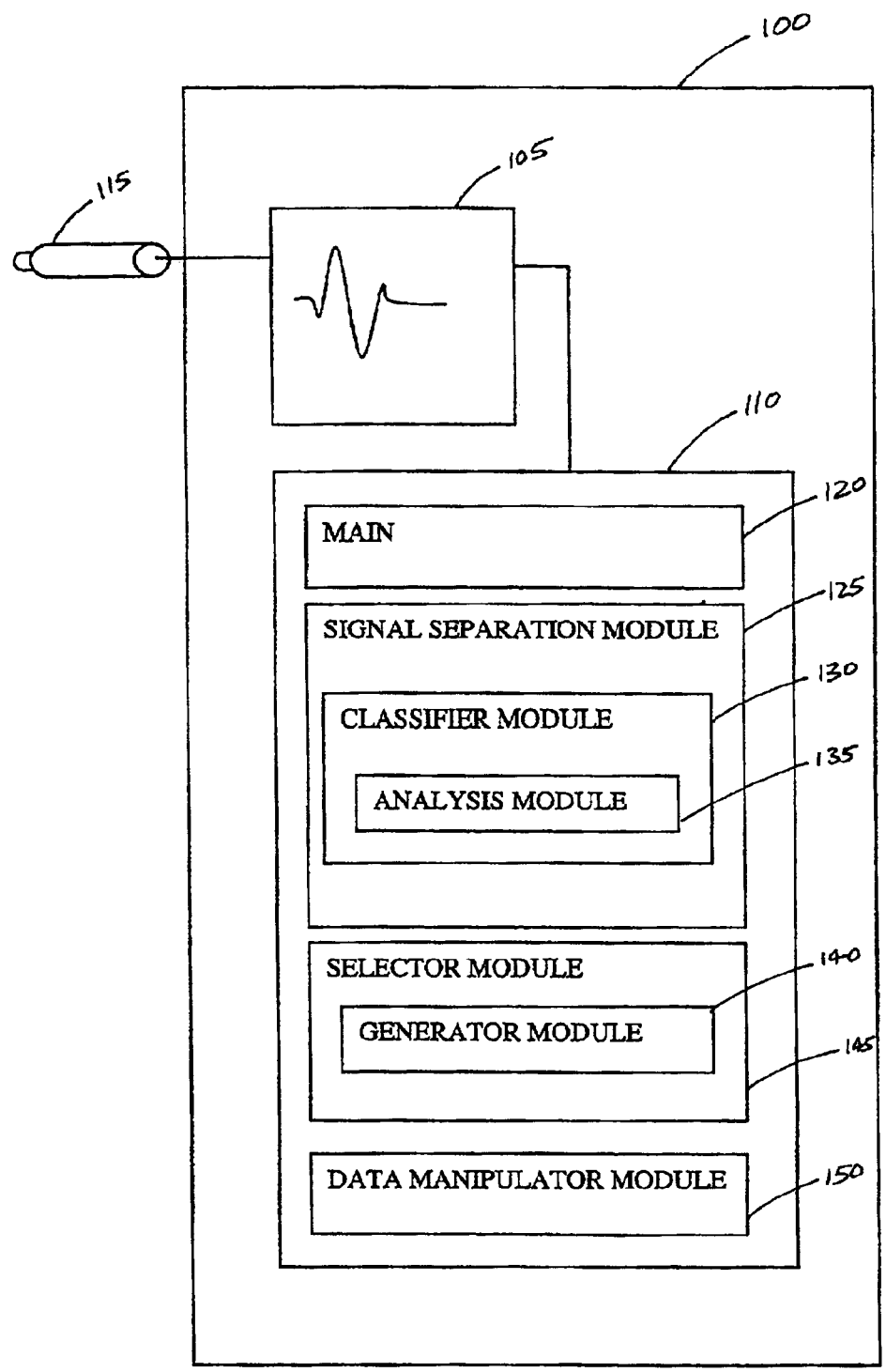
FIG. 1 shows a medical device embodying the invention.

FIG. 1 illustrates a medical device 100 embodying the invention. The medical device 100 includes a patient data acquisition device 105 and a processor 110 for implementing or running a software program. The software program is preferably stored in read-only-memory (not shown) resident in the medical device 100, but may also be stored in remote servers or a hard-drive of a personal computer, or accessed as needed from computer readable media such as a CD-ROM, magnetic disk or tape or other media. The patient data acquisition device 105 is configured to be operable to obtain ECG data from any data source or device including a ECG monitoring device, such as an electrocardiograph, a patient monitor, a Holter monitor, or a stress testing system (not shown), through a connecting link 115.

The software program 110 include several modules including a main routine 120. Once the ECG data is acquired by the patient data acquisition device 105, a signal separation module 125 of the software program 110 will be triggered by the main routine to receive the physiological data including an asynchronous component having diagnostic information and a synchronous component. The signal separation module 125 further includes a classifier module 130 to classify an abnormality condition of the diagnostic information. The classifier module 130 further includes an analysis module 135 to analyze a combination of a rhythm, for example a sinus rhythm, an atrio-ventricular conduction, a ventricular rate, a P wave amplitude, a QT interval and an age qualifier from the diagnostic information.

Based on the analysis of the diagnostic information, a generator module 140 generates a data condition of the diagnostic information. A selector module 145 then uses the data condition to select a data manipulation process. Once the selector module 145 has selected a data manipulation process, a data manipulator module 150 manipulates the asynchronous component and the synchronous component according to the data manipulation process selection.

Figure 2:
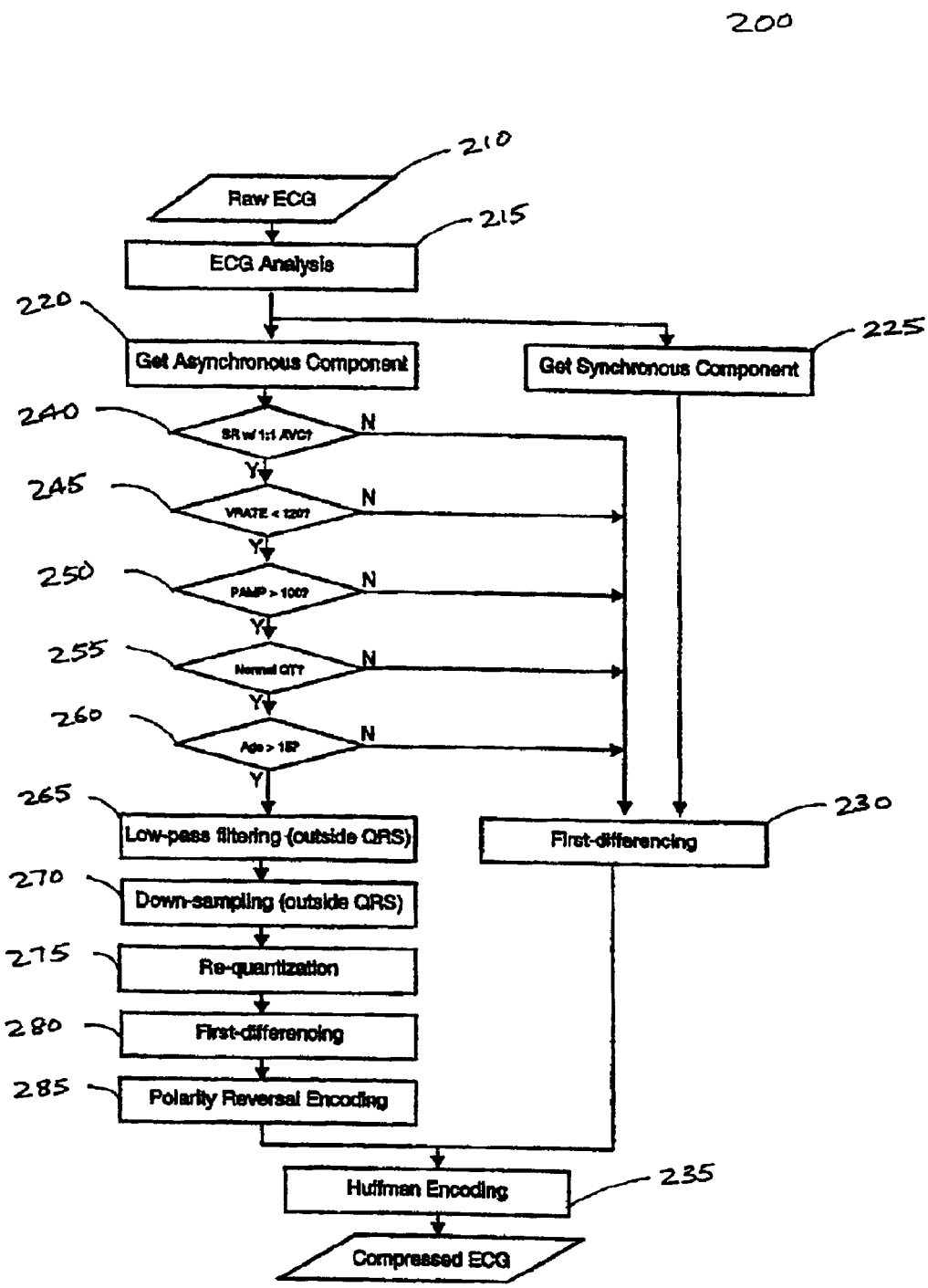
FIG. 2 shows a flow chart of a method of selecting a physiological data manipulation process according to the invention.

Referring to FIG. 2, a flow chart of a method of selecting a physiological data manipulation process 200 according to the invention includes a receiving step 210 to receive raw ECG data by from the ECG monitoring device. The raw ECG data is subsequently analyzed in the analysis module, by programs such as the 12SL brand ECG analysis software available from General Electric Co. Medical Systems Division, in an analyzing step 215 to generate a plurality of diagnostic interpretation statements to indicate a cardiac condition. The analyzing step 215 also generates a set of global measurements using the entire set of ECG leads. The measurements include a ventricular rate, an atrial rate, a PR interval, a QRS duration, a P duration, a QT interval and a set of axis of a P wave, a QRS wave and a T wave. The analyzing step 215 further generates a set of individual lead measurements including a set of amplitudes and durations of various ECG features such as P waves, Q waves, R waves, S waves, and ST levels. In addition, the analyzing step 215 also automatically generates an ECG signal quality indicator which indicates the noise level of the ECG. Furthermore, the analyzing step 215 generates a set of classification statements to indicate that an ECG is normal, borderline abnormal, or abnormal, and generates a patient information profile including the age and other relevant characteristics of the patient. However, it should be readily apparent to those of ordinary skill in the art that the analysis program can generate a different number of statements, parameters and features, and that the analysis program is not restricted to 12SL brand ECG analysis software as described herein.

Referring again to FIG. 2, the ECG data is separated into an asynchronous component in a first separating step 220, and a synchronous component in a second separating step 225. A first-difference of the synchronous component is found in a first comparing step 230. The first-difference is then Huffman encoded in an encoding step 235 to obtain lossless compressed data.

The asynchronous component obtained in the first separating step 220 is subjected to a lossy compression if it satisfies all the normal conditions. A first condition is checked at step 240. The first condition is a sinus rhythm with a 1:1 atrio-ventricular conduction and no rhythm qualifiers including normal sinus rhythm, sinus tachycardia, sinus bradycardia, and marked sinus bradycardia, and possibly rhythms with sinus or marked sinus arrhythmia, a second condition is checked at step 245. Otherwise, the asynchronous component will be subjected to a lossless compression starting in the first comparing step 230.

The second condition is a count of the ventricular rate (VRATE). If the ventricular rate is higher than 120 beats per minute (bpm), the asynchronous component will be subjected to a lossless compression starting in the first comparing step 230. If the ventricular rate falls between low to moderate, that is, less than 120 bpm, a third condition is checked at step 250.

The third condition is the presence of a P wave amplitude greater than 100 $\mu$V in all recorded leads. If the presence of a P wave amplitude greater than 100 $\mu$V in all recorded leads is not identified, the asynchronous component will be subjected to a lossless compression starting in the first comparing step 230. Otherwise, a fourth condition is checked at 255.

The fourth condition is the presence of a normal QT interval. If a normal QT interval is not present, the asynchronous component will be subjected to a lossless compression starting in the first comparing step 230. Otherwise, a fifth condition is checked in 260.

The fifth condition is a patient age. If the patient age is not greater than 15 (a preferred pediatric age limit), the asynchronous component will be subjected to a lossless compression starting in the first comparing step 230. Otherwise, the asynchronous component will be subjected to a lossy compression starting in a filtering step 265.

A moving average filter of uniform weights is used to filter the asynchronous components in the filtering step 265 to produce filtered data. The length of the moving average filter is chosen to be two or four, equaling a factor of down-sampling which depends on a down-sampling rate used in step 270. For example, the length is two if the factor of down-sampling is two, that is, the sampling rate goes from the original effective rate of 500 samples per second (sps) down to a lowered effective rate of 250 sps. The length is four if the factor of down-sampling is 4, that is, the sampling rate goes from the original effective rate of 500 sps to a lowered effective rate of 125 sps. Specifically, bimodal decimation is used in the filtering step 265 and step 270. More specifically, the asynchronous data is filtered and down-sampled selectively in time segments outside the QRS duration, while the intra-QRS region is retained at the original rate, for example, 500 sps. However, it should be readily apparent to those of ordinary skill in the art that the type of filter, and the factor of down-sampling or the decimation mode may be different than is described here due to different compatibility issues. The filtered data is then down-sampled in step 270 to produce down-sampled data.

The down-sampled data is then requantized in a quantizing step 275 to produce requantized data. A requantization reduces a resolution of the down-sampled data to a lower resolution by dropping the least significant bit (LSB) of the down-sampled data. After the requantization, the requantized data is first-differenced in a second comparing step 280 to obtain a first-differenced data. In first-differencing, a first data sample is saved, all subsequent data samples are subtracted from an adjacent data sample to yield the first-differenced data. Thereafter, the first-differenced data is encoded in a polarity reversal encoding step 285 to produce a residual signal. (When there are polarity reversals in two adjacent data samples, both of these data sample values are reduced by one least significant bit.) The residual signal is then Huffman encoded in an encoding step 235 to obtain lossy compressed data.

Various features and advantages of the invention are set forth in the following claims.

What is claimed is:

1. A method of selecting a physiological data manipulation process, the method comprising the acts of:
   receiving raw data including an asynchronous component having diagnostic information and including a synchronous component;
   separating the asynchronous component from the synchronous component; and
   selecting a data manipulation process based on the diagnostic information.

2. A method as set forth in claim 1, wherein the act of selecting of a data manipulation process includes classifying an abnormality condition of the diagnostic information.

3. A method as set forth in claim 2, wherein the act of classifying the abnormality condition includes the act of analyzing at least a one of a rhythm, an atrio-ventricular conduction, a ventricular rate, a P wave amplitude, a QT interval and an age qualifier from the diagnostic information.

4. A method as set forth in claim 1, further comprising the act of comprising the synchronous component using the lossless compression process, and the synchronous component using the lossy compression process.

5. A method as set forth in claim 4, wherein the lossy process includes the acts of low-pass filtering of the asynchronous components of the raw data to produce filtered data, down-sampling the filtered data to produce down-sampled data, requantization of the down-sampled data, comparing the down-sampled data to produce compared data, polarity reversal encoding of the compared data to produce polarity reverse encoded data, and Huffman encoding of the polarity reverse encoded data to produce lossily compressed data.

6. A method as set forth in claim 4, wherein the lossless process includes the acts of comparing the synchronous component of the raw data to produce compared data and Huffman encoding of the compared data to produce losslessly compressed data.

7. A method as set forth in claim 1, wherein the act of separating the asynchronous component from the synchronous component includes generating a data condition of the diagnostic information.

8. A method of processing physiological data, the method comprising:
   receiving raw data including an asynchronous component having diagnostic information and including a synchronous component;
   separating the asynchronous component from the synchronous component;
   selecting a data manipulation process comprising a lossy compression process and a lossless compression process based on the diagnostic information; and
   processing the asynchronous component and the synchronous component using the data manipulation process selected.

9. A method as set forth in claim 8, wherein the act of selecting of a data manipulation process includes classifying an abnormality condition of the diagnostic information.

10. A method as set forth in claim 9, wherein the act of classifying the abnormality condition includes the act of analyzing at least a one of a rhythm, an atrio-ventricular conduction, a ventricular rate, a P wave amplitude, a QT interval and an age qualifier from the diagnostic information.

11. A method as set forth in claim 8, wherein the act of processing further comprises compressing the asynchronous component with the lossy compression process, and the synchronous component with the lossless compression process.

12. A method as set forth in claim 11, wherein the lossy process includes the acts of low-pass filtering of the asynchronous components of the raw data to produce filtered data, down-sampling the filtered data to produce down-sampled data, re-quantization of the down-sampled data, comparing the down-sampled data to produce compared data, polarity reversal encoding of the compared data to produce polarity reverse encoded data, and Huffman encoding of the polarity reverse encoded data to produce lossily compressed data.

13. A method as set forth in claim 11, wherein the lossless process includes the acts of comparing the synchronous component of the raw data to produce compared data and Huffman encoding of the compared data to produce losslessly compressed data.

14. A method as set forth in claim 8, wherein the act of separating the asynchronous component from the synchronous component includes generating a data condition of the diagnostic information.

15. A medical device comprising:
   a patient data acquisition device that collects physiological data including an asynchronous component having diagnostic information and a synchronous component; and
   a software program for selecting a method of processing the physiological data, the software program including
   a signal separation module that receives the data from the data collection and separates the asynchronous component from the synchronous component; a selector module that selects a data manipulation process comprising a lossy compression process and a lossless compression process based on the diagnostic information.

16. A medical device as set forth in claim 15, wherein the signal separation module further comprises:
   a classifier module to classify an abnormality condition of the diagnostic information.

17. A medical device as set forth in claim 16, wherein the classifier module further comprises:
   an analysis module to analyze at least a one of a rhythm, an atrio-ventricular conduction, a ventricular rate, a P wave amplitude, a QT interval and an age qualifier from the diagnostic information.

18. A medical device as set forth in claim 15, wherein the lossy compression process low-pass filters, down-samples, re-quantizes, compares, polarity reversal encodes and Huffman encodes the asynchronous component.

19. A medical device as set forth in claim 15, wherein the lossless compression process compares and Huffman encodes the synchronous component.

20. A medical device as set forth in claim 15, wherein the selector module further comprises:
   a generator module to generate a data condition of the diagnostic information.

21. A software program for selecting a method of processing the physiological data, the software program comprising:
   a data collection module to collect data;
   a signal separation module that receives the data from the data collection module and separates the asynchronous component from the synchronous component; and
   a selector module that selects a data manipulation process comprising a lossy compression process and a lossless compression process based on the diagnostic information.

22. A software program as set forth in claim 21, wherein the signal separation module further comprises:
   an analysis module to analyze at least a one of a rhythm, an atrio-ventricular conduction, a ventricular rate, a P wave amplitude, a QT interval and an age qualifier from the diagnostic information.

23. A software program as set forth in claim 21, wherein the lossy compression process that low-pass filters, down-samples, re-quantizes, compares, polarity reversal encodes and Huffman encodes the data.

24. A software program as set forth in claim 21, wherein the lossless compression process compares and Huffman encodes the data.

25. A method of automatically selecting a data compression scheme, the method comprising:
   receiving raw data including an asynchronous component and a synchronous component;
   separating the asynchronous component from the synchronous component;
   classifying a data condition based on the asynchronous component; and
   selecting a data compression scheme based on the data condition.

26. A method as set forth in claim 25, wherein the act of classifying the data condition comprises classifying an abnormality condition of the asynchronous component.

27. A method as set forth in claim 25, wherein data compression scheme comprises a lossy compression process and a lossless compression process, and wherein the method further comprises the act of processing the asynchronous component using the lossy compression process and the synchronous component using the lossless compression process.

28. A method as set forth in claim 27, wherein the data compression scheme is a lossy process.

29. A method as set forth in claim 27, wherein the data compression scheme is a lossless process.

30. A medical device comprising:

a patient data acquisition device that collects physiological data including an asynchronous component having diagnostic information and a synchronous component; and a software program for selecting a method of processing the physiological data and manipulating the physiological data based on the method selected, the software program including a signal separation module that receives the data from the data collection and separates the asynchronous component from the synchronous component; a selector module that generates a data manipulation process selection based on the diagnostic information; and a data manipulator module that compresses the asynchronous component and the synchronous component according to the component type and the data manipulation process selection of the selector module.

31. A medical device as set forth in claim 30, wherein the signal separation module further comprises:

a classifier module to classify an abnormality condition of the diagnostic information.

32. A medical device as set forth in claim 31, wherein the classifier module further comprises:

an analysis module to analyze at least a one of a rhythm, an atrio-ventricular conduction, a ventricular rate, a P wave amplitude, a QT interval and an age qualifier from the diagnostic information.

33. A medical device as set forth in claim 30, wherein the data manipulation module compresses with a lossy compression process that low-pass filters, down-samples, re-quantizes, compares, polarity reversal encodes and Huffman encodes the data.

34. A medical device as set forth in claim 30, wherein the data manipulation process compresses with a lossless compression process that compares and Huffman encodes the data.

35. A medical device as set forth in claim 30, wherein the selector module further comprises:

a generator module to generate a data condition of the diagnostic information.

36. A software program for compressing physiological data, the software program comprising:

a data collection module to collect data;

a signal separation module that receives the data from the data collection module and separates the asynchronous component from the synchronous component;

a selector module that selects a data manipulation process comprising a lossy compression process and a lossless compression process based on the diagnostic information; and a data manipulator module that compresses the asynchronous component with the lossy compression process and the synchronous component with the lossless compression process based on the data manipulation process selected.

37. A software program as set forth in claim 36, wherein the signal separation module further comprises:

an analysis module to analyze at least a one of a rhythm, an atrio-ventricular conduction, a ventricular rate, a P wave amplitude, a QT interval and an age qualifier from the diagnostic information.

38. A software program as set forth in claim 36, wherein the data lossy compression process low-pass filters, down-samples, re-quantizes, compares, polarity reversal encodes and Huffman encodes the data.

39. A software program as set forth in claim 36, wherein the lossless compression process compares and Huffman encodes the data.

40. A method of automatically selecting and applying data compression scheme, the method comprising:

receiving raw data including an asynchronous component and a synchronous component;

separating the asynchronous component from the synchronous component;

classifying a data condition based on the asynchronous component;

selecting a data compression scheme based on the data condition; and compressing the asynchronous component and the synchronous component based on the data compression scheme selected.

41. A method as set forth in claim 40, wherein data compression scheme comprises a lossy compression process and a lossless compression process, and wherein the method further comprises the act of processing the asynchronous component using the lossy compression process and the synchronous component using the lossless compression process.

42. A method as set forth in claim 41, wherein the act of classifying the data condition comprises classifying an abnormality condition of the asynchronous component.

43. A method as set forth in claim 41, wherein the data compression scheme is a lossy process.

44. A method as set forth in claim 40, wherein the data compression scheme is a lossless process.

* * * * *